(12) United States Patent
Kulkarni et al.

(10) Patent No.: US 8,324,576 B2
(45) Date of Patent: Dec. 4, 2012

(54) NUCLEAR CAMERA WITH OPEN AND FLEXIBLE SOFTWARE ARCHITECTURE

(75) Inventors: Sunil Kulkarni, San Ramon, CA (US); Hugo Bertelsen, Aalborg (DK); David E. Coles, San Francisco, CA (US); Steven M. Jones, Livermore, CA (US); Douglas Murray, Castro Valley, CA (US); Jeffrey A. Hallett, Livermore, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 2280 days.

(21) Appl. No.: 09/905,418

(22) Filed: Jul. 13, 2001

(65) Prior Publication Data

US 2003/0010916 A1  Jan. 16, 2003

(51) Int. Cl.
*G01J 1/00* (2006.01)

(52) U.S. Cl. .................................. 250/336.1; 705/3

(58) Field of Classification Search ............... 250/336.1, 250/445.7; 705/3; 707/100
See application file for complete search history.

(56) References Cited

U.S. PATENT DOCUMENTS

| | | | |
|---|---|---|---|
| 4,887,211 A * | 12/1989 | Thiel et al. | 382/131 |
| 5,261,406 A | 11/1993 | MacKay et al. | 128/654 |
| 5,742,060 A * | 4/1998 | Ashburn | 250/370.09 |
| 5,760,402 A | 6/1998 | Hug et al. | 250/363.05 |
| 6,150,662 A | 11/2000 | Hug et al. | 250/363.05 |
| 6,338,030 B1 * | 1/2002 | Senn et al. | 702/189 |
| 6,505,086 B1 * | 1/2003 | Dodd et al. | 700/65 |
| 2002/0154146 A1 * | 10/2002 | Rodriquez et al. | 345/660 |

FOREIGN PATENT DOCUMENTS

| | | |
|---|---|---|
| EP | 0 297 269 A1 | 1/1989 |
| WO | WO 99/53685 A1 | 10/1999 |
| WO | WO 00/20985 A1 | 4/2000 |

OTHER PUBLICATIONS

Wang et al., Potential Use of Extensible Markup Language for Radiology Reporting: A Tutorial, Jan.-Feb. 2000, RadioGraphics, vol. 20, pp. 287-293.*

David A. Clunie, Dicom Structured Reporting, 2000, PixelMed, pp. 298-324.*

* cited by examiner

*Primary Examiner* — Christine Sung

(57) ABSTRACT

A nuclear camera is provided with an open and flexible software architecture which enables users to readily understand, modify, and exchange data files. In a constructed embodiment the software architecture utilizes xml files which can be defined and read by a user using readily available tools and viewers. Both control data and image data can be formatted in this manner. An illustrated software architecture contains a directory of manufacturer-supplied xml control files, and a directory of user modified or created xml control files. This software architecture enables users to exchange protocol and image information over conventional communications networks such as the Internet.

10 Claims, 8 Drawing Sheets

FIG. 3

Procedure ID: Gated Spect — 300
Spect Parameters

| | |
|---|---|
| Degrees in Orbit: | 301 |
| Images in Orbit: | 303 |
| Matrix Size: | 305 |
| Starting Location: | 307 |
| Rotation Direction: | 309 |
| Orientation: | 311 |
| Orbit (circular): | 313 |
| Flood Correction: | 315 |
| Acquisition Method: | 317 |

Isotope ID: 351
Patient ID: 353
View ID: 355

Processing 357

Gated Parameters

| | |
|---|---|
| No. of Gated Frames | 331 |
| % R-R Interval Variance | |
| Max % Window | 333 |
| Min % Window | 335 |
| R-R Interval Fixed | 337 |
| R-R Interval Vary | 339 |
| No. Exclude After Variance | 341 |
| Time Per ECT Azimuth or Total Beats | 343 |

| | |
|---|---|
| Time | Avg R-R |
| Frame No. | Gated Frames |
| Max Frame | Max Frames |
| Counts/Sec | |
| Beats | |

365

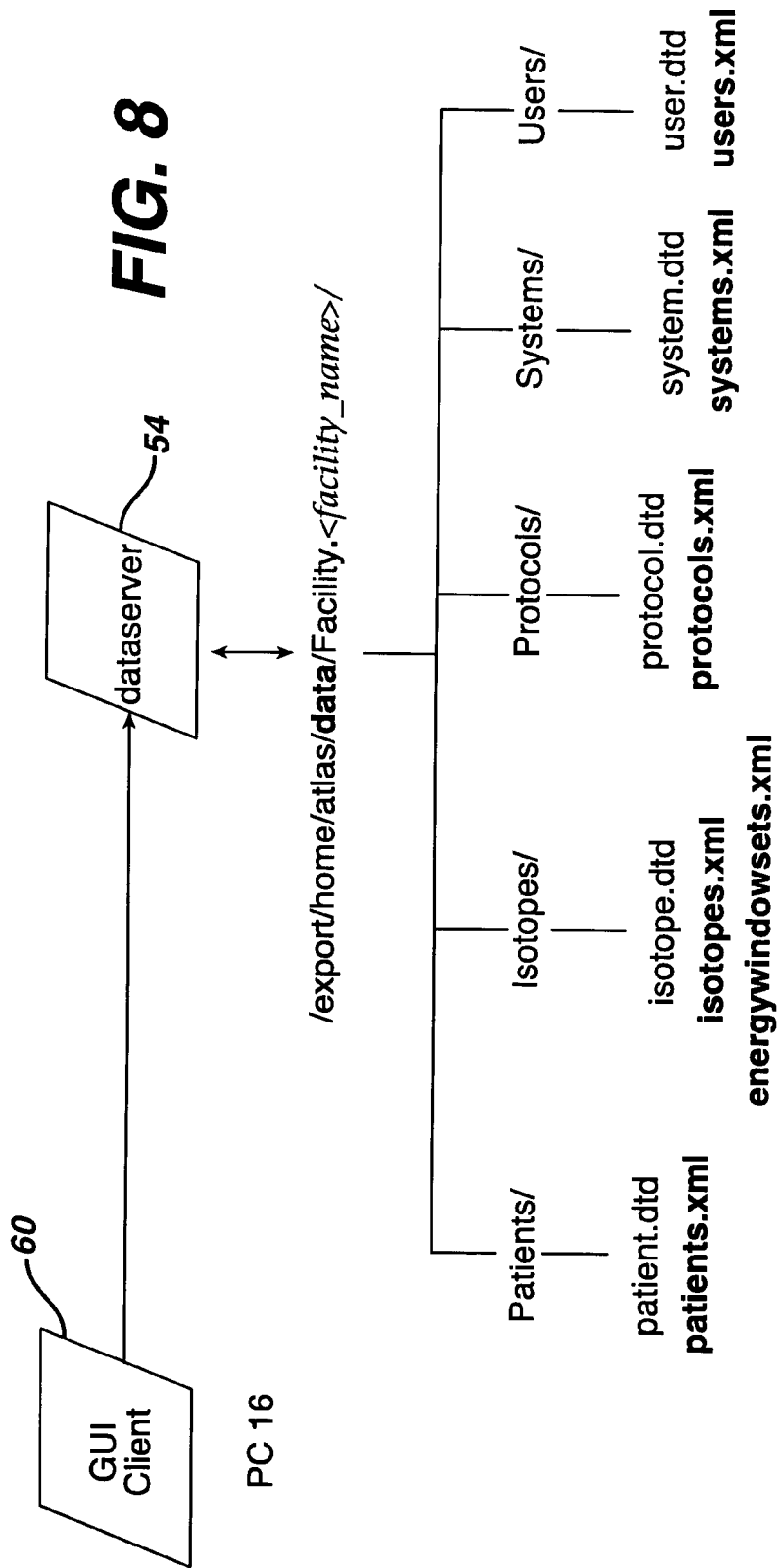

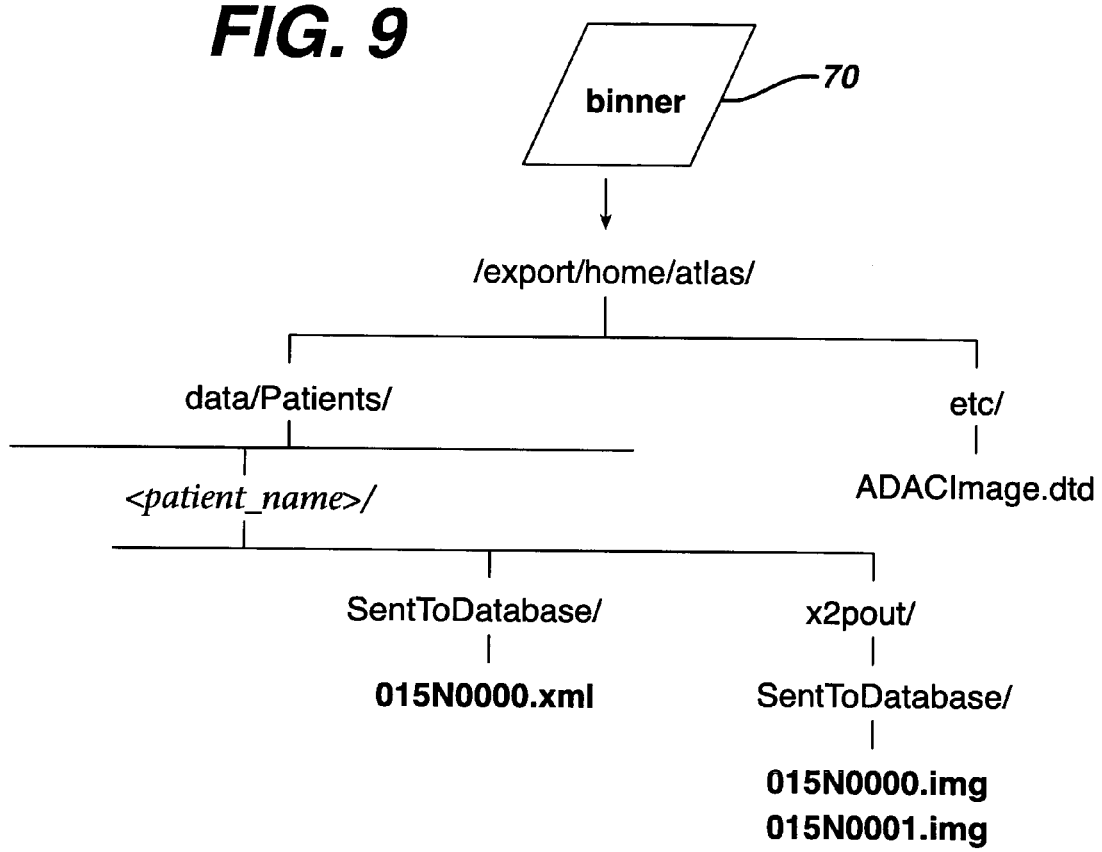

NUCLEAR CAMERA WITH OPEN AND FLEXIBLE SOFTWARE ARCHITECTURE

This invention relates to nuclear (gamma) camera imaging systems and, in particular, to nuclear cameras with software architectures which are easy to understand and readily adapted to changing needs of clinicians.

Traditionally, medical image data obtained from medical imaging systems such as nuclear cameras, computed tomography scanners, magnetic resonance imaging systems and ultrasound has been defined by proprietary image data formats developed by the various system manufacturers. Such proprietary image formats mean that the images produced by the different systems must be viewed or displayed by proprietary viewing/display applications provided by each vendor. A user is effectively locked into using the particular manufacturer's proprietary formats. Images produced by one imaging system cannot be readily viewed on another manufacturer's system. Realizing these limitations, the NEMA trade organization has organized and defined an image format which all manufacturers can use, known as the DICOM (Digital Imaging and COmmunication in Medicine) standard. The various manufacturers of medical imaging equipment can provide translators by which their proprietary formats can be converted into a common format in which users can exchange and view images on a variety of different display devices.

Data format standards such as DICOM have not fully solved the problems of incompatibility and ease of use, however. First of all, a user of a particular system must have access to conversion routines by which a manufacturer's proprietary image format can be translated into the standard format. Conversion routines are not always readily available or universally successful in their operation. Secondly, the proprietary image data formats are typically inflexible with respect to changes. Changes are often desirable to enable a clinician to satisfy new user requirements, or incorporate innovations into an application, use or operation of the medical imaging system, or to enable the use of new software technologies that improve the performance of the medical imaging system. Thus, proprietary image formats have the effect of limiting innovation in imaging by clinicians and thwarting improvements to clinical productivity.

Furthermore, while image data standards such as DICOM enable users to exchange and use images from the medical imaging systems of different manufacturers, these standards are only effective when all manufacturers agree upon the standards and their requirements. The need for common agreement upon standards means that changes to standards cannot be made quickly and easily. Proposed changes need to be discussed, commented upon, and agreed to by the manufacturers before being implemented for the benefit of end users. Accordingly it is desirable for a medical imaging system to have a software architecture which overcomes these obstacles and readily accommodates advances in efficiencies and techniques as they are developed by the medical community.

In accordance with the principles of the present invention a nuclear camera software architecture is described which addresses these deficiencies of proprietary and standard formats. The software architecture of a camera of the present invention allows the operation and performance of the camera to be readily modified by users. Modified data can be easily exchanged because of the self-descriptive nature of the software language and the ability to provide readily available format descriptions to all users. In a preferred embodiment the software architecture embraces an open format which is publicly available. In a constructed embodiment of the present invention the software architecture of the nuclear camera uses extensible Markup Language (XML) which is an open format that enables changes to the data format to be made by users and other manufacturers alike. The inventive software architecture presents data that is self-describing in that relationships between various pieces of data are captured in the format definition used to store and interpret the data. In a preferred embodiment, both image data and nuclear camera control information, in particular, study protocols, are defined in the open, extensible software architecture, enabling users to exchange not only new image data formats but also new system control procedures.

In the drawings:

FIG. 3 illustrates a gamma camera protocol setup screen for a gated SPECT study;

FIGS. 6-9 illustrate the directory structure of the software architecture of a preferred embodiment of the present invention.

Figure 1:
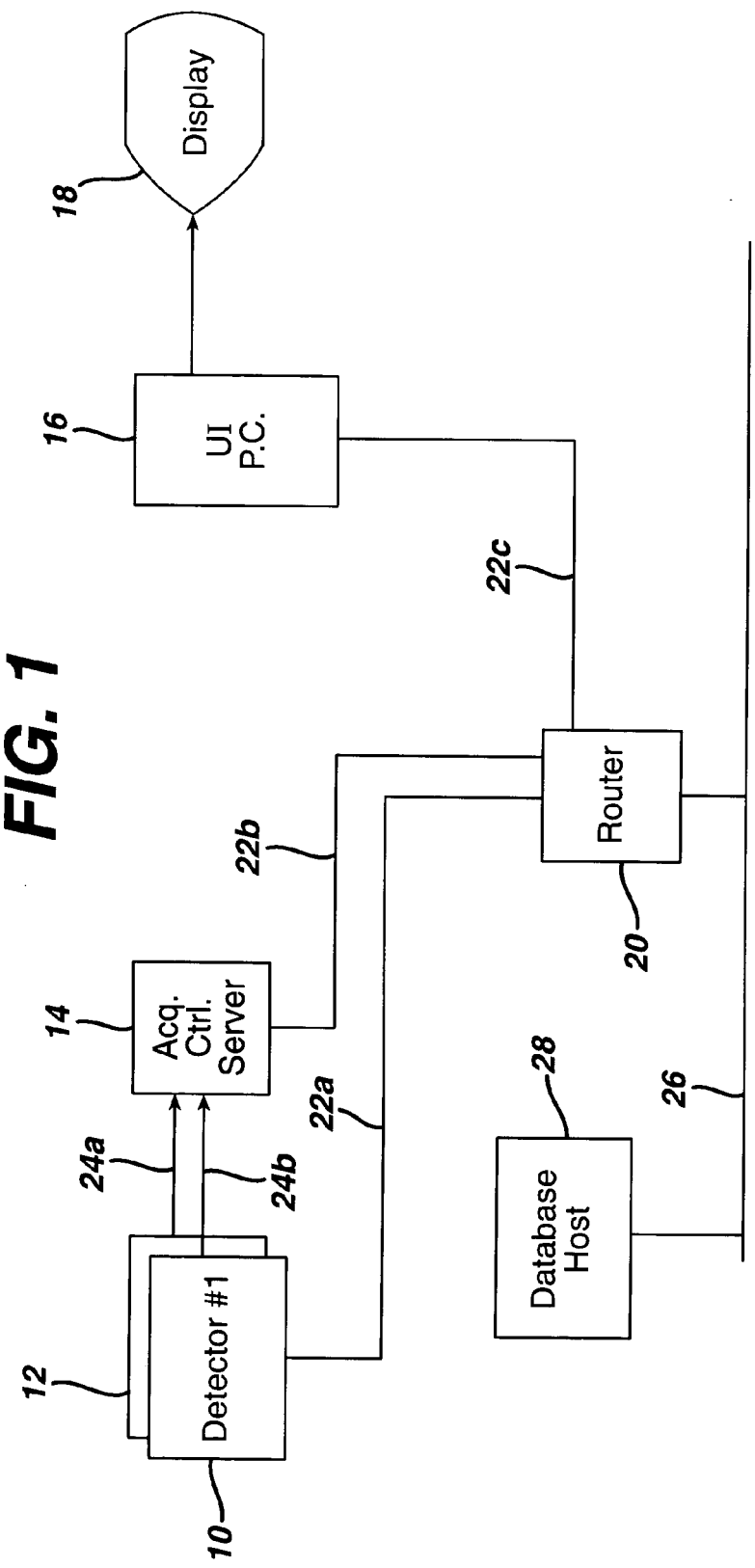
FIG. 1 illustrates in block diagram form a gamma camera constructed in accordance with the principles of the present invention.

Referring first to FIG. 1, a gamma camera constructed in accordance with the principles of the present invention is shown in block diagram form. A software architecture of the present invention may be used with either a single detector gamma camera, or with a dual detector gamma camera such as those shown in U.S. Pat. No. 5,760,402 (Hug. et al.) or 6,150,662 (Hug et al.). The dual detector cameras shown in these patents are commercially available as the Forte™ and Skylight™ gamma cameras from ADAC Laboratories of Milpitas, Calif. These camera systems include one or more detectors 10, 12 which sense scintillation events and transfer event data over a high speed serial bus 24a, 24b from each detector to an acquisition control server 14. The acquisition control server 14 bins the event data into images, which are then sent by way of a router 20 to a database host 28 connected to a department Ethernet 26. The database host 28 is the computer on which the acquired images are normally saved. The database host is also the processing and viewing station where 3D reconstruction, re-slicing and presentation of the processed images to the user is performed. The router 20 serves to isolate internal camera data traffic from more varied departmental data traffic. A user interface personal computer 16 is coupled to the acquisition portion of the gamma camera by the router 20 and an Ethernet network 22a, 22b, 22c. The p.c. 16 controls and monitors the image data acquisition and may perform additional image processing and display functions using an image display 18. P-scope and energy spectrum data may be displayed to the user on the display 18, enabling the user to position the patient properly in front of the camera, set energy windows correctly, and review acquired data, for instance.

Figure 2:
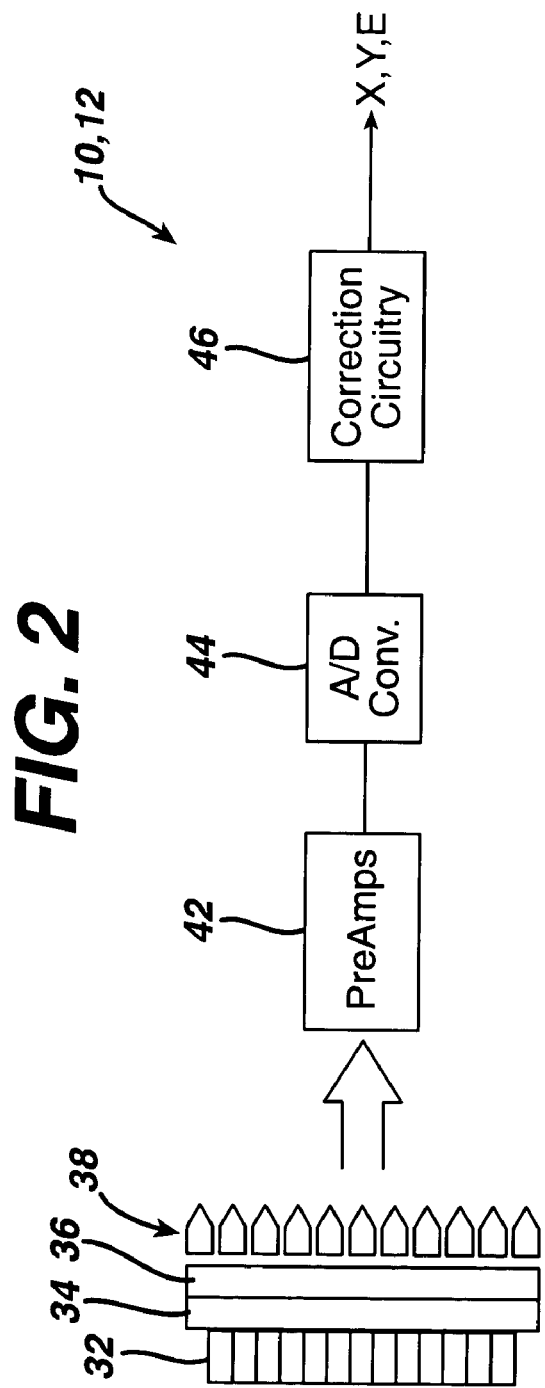
FIG. 2 illustrates the detector of a gamma camera in block diagram form.

A camera detector is shown in greater detail in FIG. 2. As is well known in the art, a gamma camera detector is composed of a collimator 32, a scintillation crystal 34, and a lightguide 36. The photons produced by the crystal 34 and guided through the lightguide 36 are received by an array of photomultiplier tubes (PMTs) 38. A scintillation event is usually received over an area covering several PMTs, and the outputs of the tubes are sensed and used to locate the position on the detector at which the radiation event was received. The PMT output signals are amplified by pre-amplifiers 42 and digitally sampled by A/D converters 44. The samples from each PMT are accumulated for the duration of a scintillation event and, since multiple PMTs are involved in the detection of a single event, the accumulated outputs of multiple PMTs are accumulated to acquire the overall energy signal for a particular scintillation event. The detected energy data and location data from each scintillation event is modified by correction circuitry 46, which produces the detector outputs for energy (E) and event location (X,Y). The event data is then binned for image processing.

The p.c. 16 and user interface display 18 allow a user via keyboard and/or pointer control to select or create a predefined set of parameters (or protocols) for direction of a SPECT imaging session or other selected study by the gamma camera system. FIG. 3 illustrates a parameter interface screen and configurable parameters of a nuclear camera system for data acquisition that are selected and displayed on a screen by the user. FIG. 3 illustrates some of the parameters that are configurable by the user for a desired study. It is appreciated that once set, the configurable parameters can be saved and referenced in a computer file for subsequent recall. The stored parameters or protocol file can then be recalled and utilized for another study, thus eliminating the need to again enter the parameters for similar or identical studies. The name of the parameter file shown in FIG. 3 is "GATED SPECT" and is indicated at 300. It is appreciated that the acquisition system, once instructed by the user, will relay the parameters set by the user to the camera in order to initialize and begin a particular study. The initiation is done by selection of processing command 357. A user interface of this type is thus versatile while at the same time providing a high degree of automation of the execution of selected study protocols.

Figure 4:
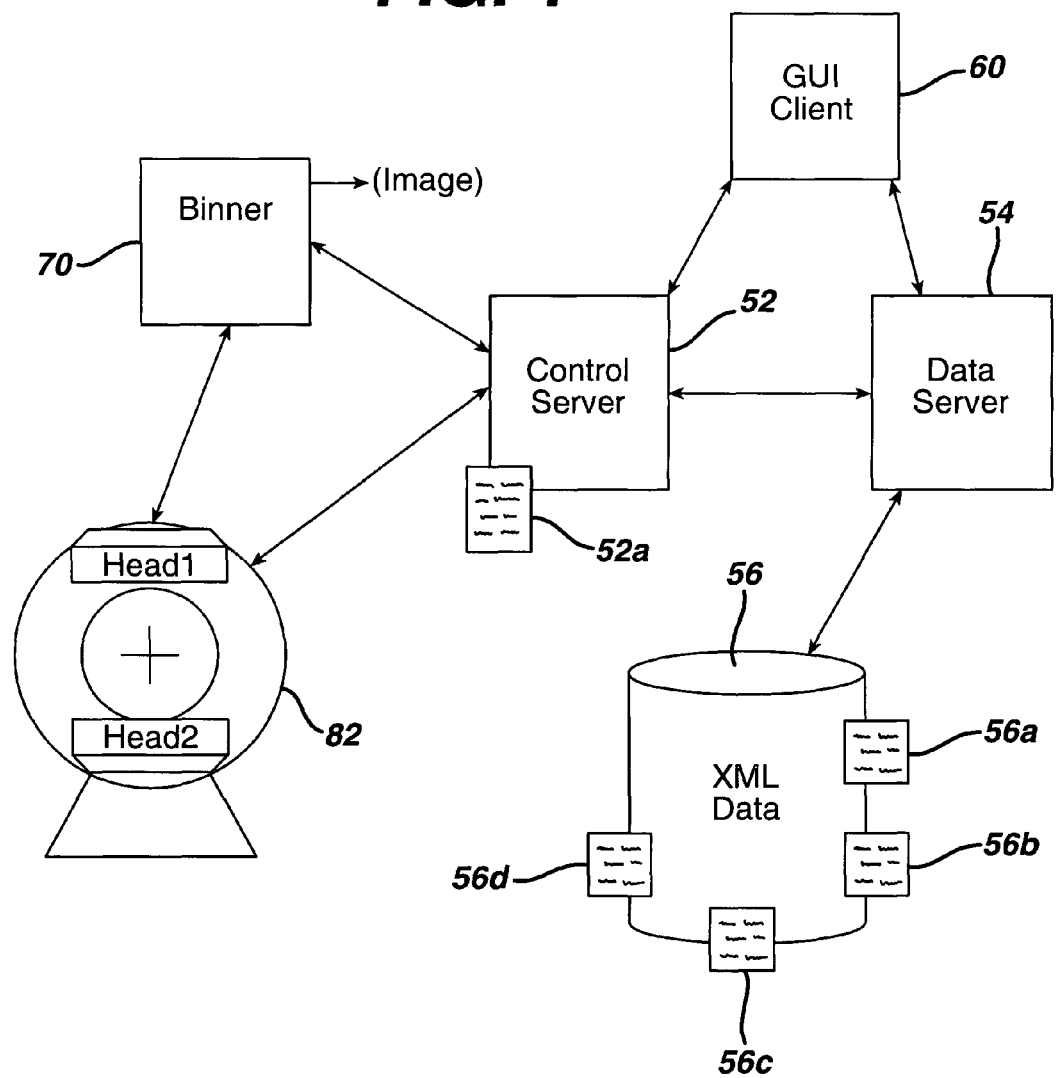
FIG. 4 illustrates the flow of control and image data in a gamma camera constructed in accordance with the principles of the present invention.

FIG. 4 illustrates the flow of control and image data in a gamma camera constructed in accordance with the principles of the present invention. Located on the acquisition control server hardware 14 are a control server 52 and a data server 54. These servers act to access and process data stored on an xml data storage device 56. The data stored on the device 56 includes patient schedule data 56a, protocol data 56b, isotope data 56c, and collimator data 56d. This data is used to operate and control the gamma camera 82. In a preferred embodiment this data is stored in xml format as explained more fully below. The control server uses the data stored on the device 56 and executes programs 52a called "scripts," also stored on the xml data storage device 56, to control the operation of the gamma camera 82. The control and data servers both operate under user control through a graphical user interface (GUI) client application 60 which runs on the user interface p.c. 16.

In operation the user defines a study (exam) by associating a protocol with a particular patient through the GUI client 60. The protocol comes from the data server 54. The GUI client then sends the study to the control server 52. The protocol for the study has a script name attached to it, enabling the control server to identify the script to execute within its interpreter. The script is executed to carry out the protocol, performing calculations as needed, and can obtain certain protocol parameters from the user such as number of azimuths, time per frame, and so forth. The script also prompts the user at various points during the study for further input as needed, such as selection of a point of interest to be tracked by the detectors as they rotate about the patient.

In a constructed embodiment the scripts are written in a scripting language called EASL. EASL was developed by the assignee company of the present invention using readily available tools for writing scripting language such as LEX and YACC. YACC is a UNIX-based tool which enables a programmer to compile the grammatical terms used in EASL to interpret the scripts. The EASL program is an interpreter for the scripts, which in turn use the xml files, and is stored in the control server 52.

The event data produced by the camera detectors Head1 and Head2 in this example is processed as described above and transferred to a binner 70. The binner interacts with the control server 52 to format image data in an xml format. The formatted image data is then further processed, transferred or stored as described more fully below.

Figure 5:
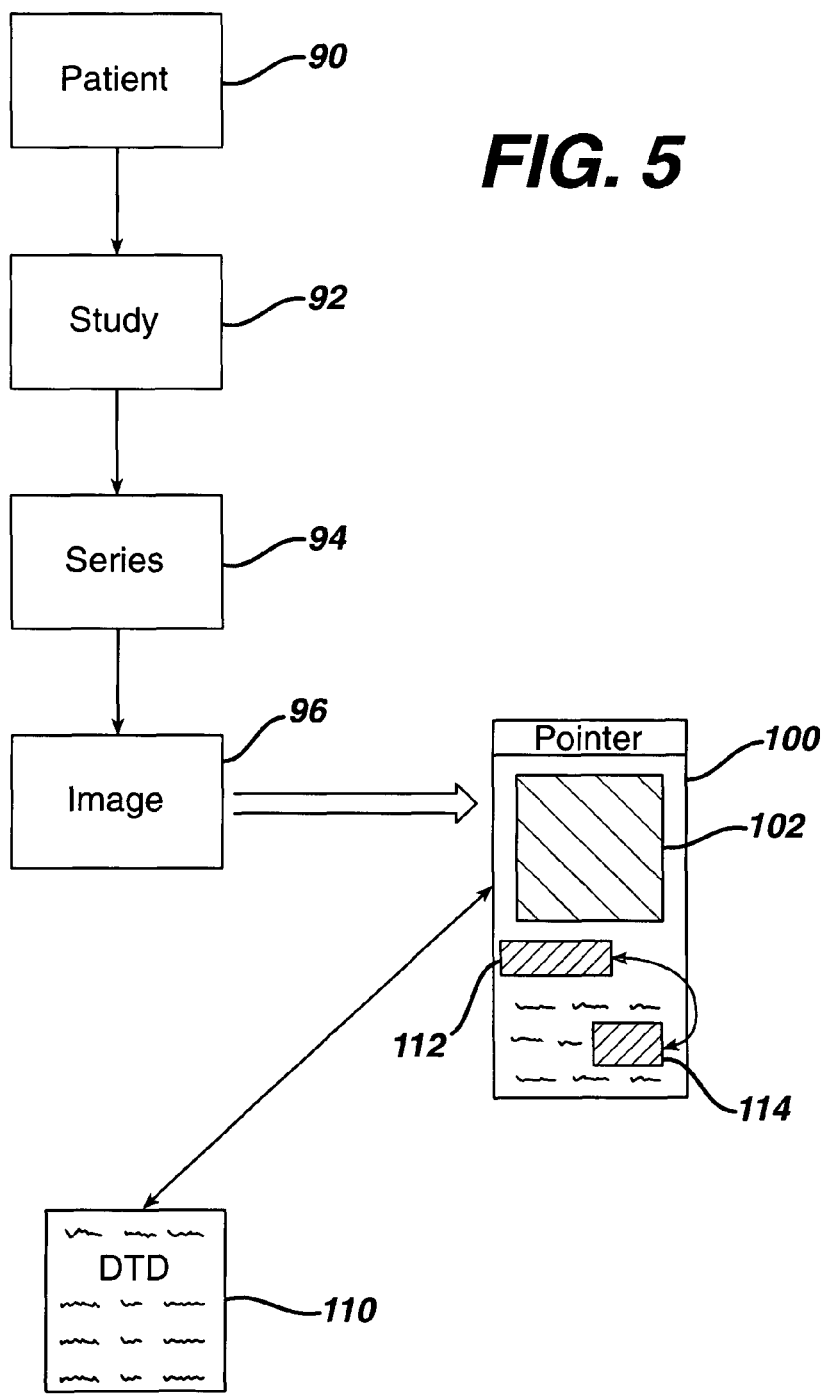
FIG. 5 illustrates the organization of patient data in a constructed embodiment of the present invention.

FIG. 5 illustrates one form of organization of an xml image file. The image file includes information about the image such as the identification 90 of the patient, the nature of the nuclear study 92 which produced the image, the series 94 of the study, and the image information 96. In the illustration this information is all contained in an xml image file 100 referred to in this example as <ADACImage.xml>. The file includes the patient and study information just described, and the image data shown as 102. The file may contain other pieces of information 112, 114 which relate to the image and may also relate to each other. The meanings of these pieces of information and their relationships are captured in a definitional file called a Document Type Definition 110 (DTD) file. The image file 100 has a pointer to the DTD file 110 by which a processor or viewer can access the DTD file and interpret the information in the image file. The pointer can be to another file or directory running on the gamma camera as described below. The pointer can also be the URL of a location where the DTD file can be found. For example, if the image is being viewed by a browser, the browser will consult the DTD at the noted URL on-the-fly, and thus be able to interpret and understand the pieces 112, 114 of information which are stored in the image file 100.

An example of an <ADACImage.xml> file is shown in Appendix 1 below. It is seen that the second line of the file contains the pointer to the DTD file ADACImage.dtd which defines the relationships of the data elements in the xml image file. The initial portion of the file contains information of the type shown at 90-94, including the equipment and detector used, the reconstruction processing used, patient information, isotope dose, and so forth. Toward the end of the file is a block of frame pixel information.

The initial portion of a DTD file which interprets the <ADACImage.xml> file is shown in Appendix 2. This <ADACImage.dtd> file is pointed to in the second line of the <ADACImage.xml> file and provides instructions to a reader as to the interpretation of the <ADACImage.xml> file. This particular DTD file begins with information as to the purpose, creation, and revision history of the DTD file. This is followed by a definition of the various elements of the image.xml file. The <ADACImage.xml> file is written in accordance with the rules set forth in the <ADACImage.dtd> file.

The xml files are seen to be written in easily understandable grammatical terms. With xml files a user is able to make changes to the xml file structure, adding user-desired information to the data already produced by the camera system. The user is able to make changes to algorithms executed by the scripts such as study protocols carried out by the gamma camera. The grammar-based nature of the xml files makes it easy to add newly defined xml files or to change existing ones, for instance, to create custom study protocols. Image files can be modified by a hospital user, for instance to add the hospital's unique codes and information such as accession numbers to image data. The DTD file referenced by an image would in that case define the relation of the accession number to a particular image and patient. Since xml is an open format the ability to make these changes is available to all users. In most instances these changes are evident in the xml files themselves due to the self-describing nature of the xml and DTD files, with the format defining how the different elements in the data relate to each other. The xml-formatted files can be viewed on a browser or on a text editor which reveals the grammatical text of the files. The xml files can also be viewed with commercially available xml viewers such as xmlspy. The relationships of the elements of the file can be viewed in this way as the hierarchy of relationships is shown automatically by the viewer. A particular application can thus make use of all of the relationships defined for the data.

A portion of another example of an xml file, <protocol.xml>, is shown in Appendix 3. The <protocol.xml> file has a script name attached to it to enable the gamma camera to carry out a study protocol called "MIBI." Within a protocol are various steps, each representing a different acquisition step, e.g., for a static image, a stress cardiac study, or a whole body study. In the illustrated <protocol.xml> file the different characteristics of the study are called "TRAITS," which are interpreted and defined by the "protocol.dtd" file referred to by the <protocol.xml> file. Typical TRAITS include such characteristics as the detector rotation, the time at each detector orientation, the frames acquired at each step, and the isotope dosage used. The defined TRAITS are then used in the steps of the protocol identified in the file as <acquisitionstep>.

Appendix 4 illustrates an EASL script called "tbbase.asl" for conducting a total body nuclear study. The illustrated script is written in the EASL scripting language referred to above. The script is seen to include comment lines which make the script easily understandable to users. The script is also seen to control the prompts and messages displayed to the user on the GUI as the study proceeds. In a gamma camera of the present invention a script is loaded into the interpreter and is used to run the protocols which control the operation of the camera.

Figure 6:
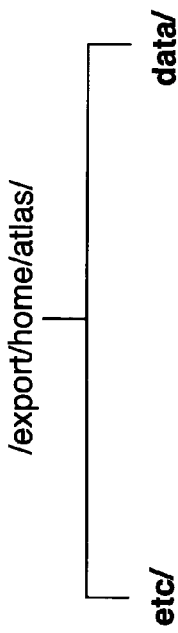

Examples of the directory hierarchy of the files stored on the data storage device 56 are shown in FIGS. 6-9. In these examples the directory /export/home/atlas/ contains two types of data as shown in FIG. 6. Software shipped with the gamma camera by the manufacturer is stored in the etc/directory. This includes configuration files, default protocols, default users, default isotopes, collimators, and so forth. This is primarily data used by the control server 52, the data server 54, and the binner 70, and comprise a complete set of files necessary to operate the gamma camera. A data/directory is also provided for storage of data created by the user. This includes acquired image data, user defined protocols, schedules of patients, isotopes, energy window settings, and other files created or modified by the user.

Figure 7:
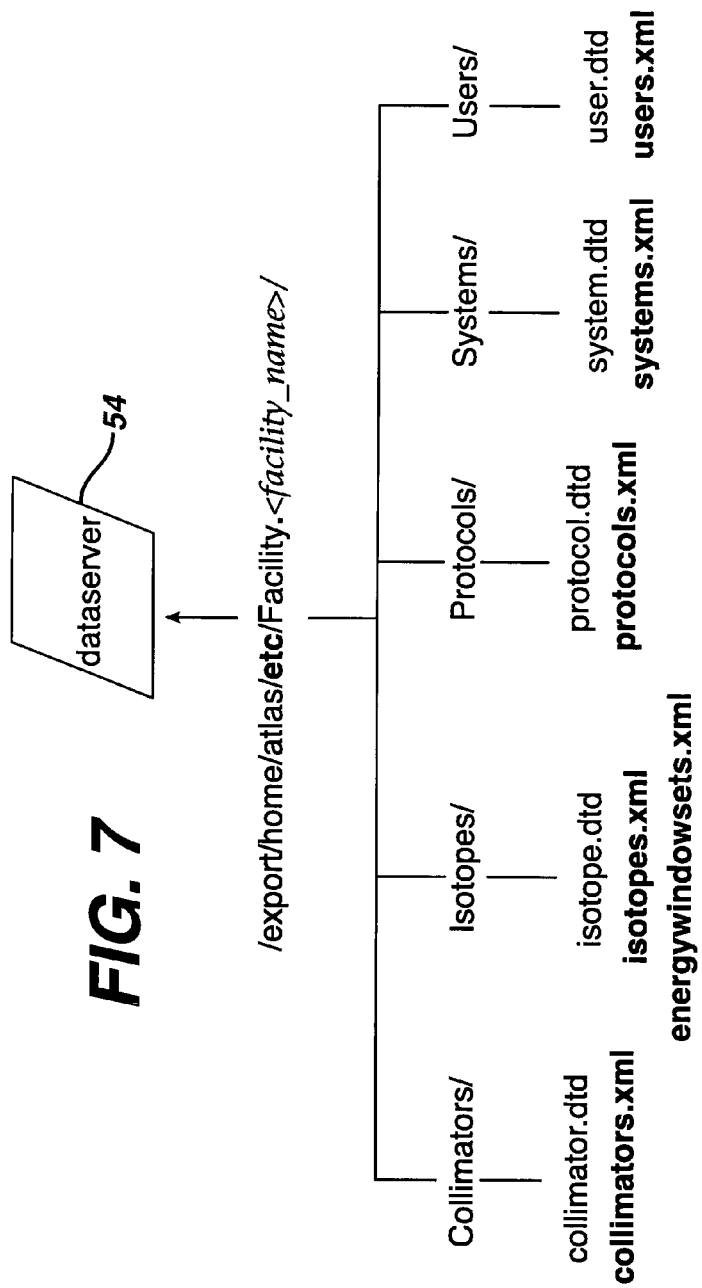

FIG. 7 shows further details of the manufacturer-supplied directory etc/. The collimators.xml file contains a list of all collimators supported by the camera. Isotopes.xml and energywindowsets.xml contain lists of isotopes and their physical properties and default energy window settings. Protocols.xml contains a list of standard study protocols. Systems.xml contains a list of systems used by the camera, and whether they are clients or servers. Users.xml contains a list of default users for the camera.

The directory data/ for user-created data is shown in FIG. 8. This directory has files corresponding to those of the etc/directory, but in this case the files are those which have been created by or modified by a user. For instance, a user may take a manufacturer-supplied protocol and modify it for a particular study which the user desires to perform. The modified protocol is stored as a protocols.xml file in the data/directory and can be called up and executed by the user each time the user wants to conduct that study. The user-created data takes precedence over the manufacturer-supplied data. Any time a client asks for data from the data server 54, the server will first access the data/directory to see if a user-created file satisfies the request. Only if no user-created file is found will the server look for a file in the etc/directory.

Both directories are seen to store DTD files corresponding to the xml files, which are used to interpret the definitions in the corresponding xml files. The patient.dtd file, for instance, defines how the patient visit and study information is written out, that is, the format and relationship between the various pieces of information contained in the patients.xml file. Similarly, protocol.dtd defines how the protocol information is written out and interpreted. A DTD file is used to view an xml file when using an xml viewer such as xmlspy, or alternatively a text editor can be used to view the xml file in the form shown in the appendices.

FIG. 9 illustrates the production and storage of an image.xml file by the camera. The binner 70 writes out the results of a particular study in xml format when acquisition is completed for a given acquisition step of a protocol. The image.xml file is written by the binner in accordance with the rules in the ADACImage.dtd file. This example shows an image file 015N0000.xml which has been stored under a particular patient's name, <patient_name>/, under the data/Patients/directory. Image.xml files are translated with the help of an "xml2peg" translator program into an image format 015N0000.img and stored under an x2pout/directory. This directory is accessed by the database host 28 in response to an external user request for the patient's images. When a particular image has been exported to the database host, the image is then stored under the SentToDatabase/directory and a confirmation of the export is sent as a status update to the data server 54. Thus, images are available in both an xml format and in an image format which is most efficient for storage, transport or display by the database host.

What is claimed is:

1. A radiation based diagnostic imaging system including:
a detector which acquires radiation data;
an image processor which processes the radiation data to produce image data;
a control data storage medium, coupled to an acquisition controller, which stores control data in an xml format; and
the acquisition controller executes a script utilizing an xml file to control the acquisition of the radiation data.

2. The system of claim 1, wherein the xml file utilized by the script is a protocol file of the form <protocol.xml>.

3. A diagnostic imaging system including:
a detector which acquires diagnostic data;
an image processor which processes the diagnostic data to produce image data;
an acquisition controller which controls the detector to acquire diagnostic data;
a control data storage medium, coupled to the acquisition controller, which stores control data in xml format;
an image data storage medium, coupled to the image processor, which stores image data in xml format; and
a server coupled to the control data storage medium and the image data storage medium, which server accesses at least one of xml control data files and xml images data files and executes scripts which utilize xml control data files.

4. A nuclear camera system comprising:
a detector which acquires radionuclide event data;
an image processor which processes the event data to produce image data;

an acquisition controller which acts to control the detector to acquire event data in accordance with a study protocol, wherein the acquisition controller executes a script utilizing an xml file to control the acquisition of event data; and a control data storage medium, coupled to the acquisition controller, which stores control data in an extensible and open data format.

5. A nuclear camera system comprising:

a detector which acquires radionuclide event data;

an image processor which processes the event data to produce image data;

an acquisition controller which acts to control the detector to acquire event data in accordance with a study protocol;

a control data storage medium, coupled to the acquisition controller, which stores control data in xml format, the control data comprising xml files provided by the camera system manufacturer and xml files modified or created by a camera user; and a user interface and a server, responsive to the user interface and coupled to the control data storage medium and the image data storage medium, which accesses xml control data files or xml image data files in response to user commands wherein the server executes scripts which utilize xml control data files.

6. A method of acquiring nuclear medicine images comprising:

acquiring emission data from an imaged subject;

processing the emission data to produce image data;

storing the image data; and incorporating new user data format requirements into the processing data without requiring a manufacturer's proprietary image format conversion routine;

wherein the image data is stored in a format that allows for such incorporation of new user data format requirements.

7. The method of claim 6 wherein the image data is stored in xml format.

8. The method of claim 6 further comprising controlling acquisition of the emission data with scripts written in an open and extensible format.

9. An medical imaging system comprising:

means for acquiring emission data from an imaged subject;

means for processing the emission data to produce image data;

means for storing the image data; and means for incorporating new user data format requirements into the processing data without requiring a manufacturer's proprietary image format conversion routine;

wherein the image data is stored in a format that allows for such incorporation of the new user data format requirements.

10. The medical imaging system of claim 9 wherein the image data is stored in xml format.

* * * * *